(12) United States Patent
Firestone et al.

(10) Patent No.: US 7,115,277 B2
(45) Date of Patent: *Oct. 3, 2006

(54) METHOD FOR ENABLING DELIVERY OF AN ACTIVE AGENT

(75) Inventors: Bruce A. Firestone, Irvine, CA (US); Thao Tran, Fountain Valley, CA (US); Teresa G. Joshi, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 341 days.

This patent is subject to a terminal disclaimer.

(21) Appl. No.: 10/308,295

(22) Filed: Dec. 2, 2002

(65) Prior Publication Data

US 2003/0113370 A1 Jun. 19, 2003

Related U.S. Application Data

(63) Continuation-in-part of application No. 09/760,133, filed on Jan. 12, 2001, now Pat. No. 6,656,500, which is a continuation of application No. 09/262,623, filed on Mar. 4, 1999, now Pat. No. 6,248,354.

(51) Int. Cl.
*A61K 9/48* (2006.01)
*A61K 9/66* (2006.01)

(52) U.S. Cl. .................... 424/451; 424/452; 424/455; 514/432; 705/2

(58) Field of Classification Search ................. 424/45, 424/451–455; 705/2
See application file for complete search history.

(56) References Cited

U.S. PATENT DOCUMENTS

| | | | | |
|---|---|---|---|---|
| 4,532,133 A * | 7/1985 | Schmidt | .................... | 514/725 |
| 4,612,194 A * | 9/1986 | Ismail | ....................... | 424/752 |
| 5,594,637 A * | 1/1997 | Eisenberg et al. | ............. | 705/2 |
| 5,619,991 A * | 4/1997 | Sloane | ....................... | 600/300 |
| 6,001,885 A * | 12/1999 | Vega et al. | .................. | 514/725 |
| 6,045,501 A | 4/2000 | Elsayed et al. | | |
| 6,248,354 B1 * | 6/2001 | Firestone et al. | ........... | 424/451 |
| 6,315,720 B1 | 11/2001 | Williams et al. | | |
| 6,437,003 B1 * | 8/2002 | Roullet et al. | .............. | 514/725 |
| 6,582,721 B1 * | 6/2003 | Lang | .......................... | 424/439 |
| 2002/0016532 A1 | 2/2002 | Elsayed et al. | | |

* cited by examiner

*Primary Examiner*—Michael G. Hartley
*Assistant Examiner*—Micah-Paul Young
(74) *Attorney, Agent, or Firm*—Walter A. Hackler

(57) ABSTRACT

A method for enabling deliver of an active agent is provided which includes the preparation of doses of the active agent distributing educational materials and guidelines for counseling patients with regard to what the patients need to know and what the patients must do in order to both avoid adverse side effects while taking the dose and to receive prescriptions for the doses.

25 Claims, 1 Drawing Sheet

METHOD FOR ENABLING DELIVERY OF AN ACTIVE AGENT

The present application is a continuation-in-part of U.S. Ser. No. 09/760,133 file Jan. 12, 2001 now U.S. Pat. No. 6,656,500 B2 which is a continuation of U.S. Ser. No. 09/262,623 filed Mar. 4, 1999 now U.S. Pat. No. 6,248,354 B1.

The present invention generally relates to a method for enabling delivery of an active agent, or drug, to a patient. More particularly, the present invention is directed to a method for enabling delivery of an active agent, or medicament, having low aqueous solubility. Still, more particularly, the present invention is directed to a method for enabling delivery of a low aqueous soluble active agent while avoiding occurrences of known or suspected side effects of the active agent.

A low aqueous solubility of a great number of active agents is a source of inconvenience and further raises the overall cost of a course of treatment with any such low solubility medicament. Low aqueous solubility of an active agent often leads to low and unreliable systemic bioavailability.

Retinoids, that is, functional and structural derivatives of retinoic acid, have been successful in the treatment of acne, particularly nodular acne, psoriasis, disorders of Keratinion and oncology. However, the low aqueous solubility has limited the administration of the retinoids to their use in topical gels, creams, orals and the like.

A desired advantage of oral administration of retinoids is increased efficacy. Thus, in general, while the advantages or oral delivery or topical delivery of active agents are well known, oral administration of retinoids is made difficult by their low aqueous solubility, which results in decreased effectiveness in systemic drug delivery.

As set forth in an article by Humberstone and Charman, entitled, "Lipid-based Vehicles for the Oral Delivery of Poorly Water-Soluble Drugs", (Adv. Drug Del. Reviews 25, 1997, pp. 103–128), there are few commercial examples of lipid-based oral formulations, other than special cases, as for example, eyclosporin and the lipid-soluble vitamins. Reasons for the lack of commercial success include the complexity of the interfacial and physical chemistry. The article also reported that the results of different lipids and bioavailability are very drug specific. Accordingly, while the article appears to set forth general principles including emulsification techniques, there is, in fact, no general guidelines which can be relied on for developing an oral system for the delivery of a specific active agent, such as a retinoid, having low aqueous solubility.

In addition, many retinoids are known to or are suspected of producing adverse side effects in certain individuals. Such side effects include weakness, rash, muscle pain, joint pain, joint disorder, increased blood levels of Creatine Phosphokinase, nose dryness, dizziness, nosebleed, dry eye, hair loss, elevated blood levels of fatty acids, increased muscle tone, anxiety, emotional instability, burning or tingling sensation to the skin, body pain, back pain, depression, diarrhea, acne, skin disorder, foot pain, abdominal pain, neck pain, dry mouth, dilated blood vessels, knee pain, infection, neck stiffness, pelvic pain, arm pain, chills, dandruff, leg pain, irregular heartbeat, increased blood pressure, migraine, fainting, increased heart rate, loss of appetite, gas, vomiting, stomach disorder, irritation in the mouth, purplish red spot on the skin, decreased number of blood platelets, abnormal white blood cell count, anemia, decrease in white blood cell count, abnormal platelets, increased cholesterol, increased blood levels of lactic dehydrogenase (the study doctor can explain this), swelling, thirst, protein in the urine, increased blood levels of amylase (the study doctor can explain this), bone pain, arthritis, bone disorder, muscle weakness, trouble sleeping, sleepiness, forgetfulness, sensing that either the body or the surroundings are moving, inflammation of the throat, inflammation in the nose, sore throat, inflammation of the sinus, skin redness from the sun, burning sensation on skin, skin burn, skin peeling, irritated skin, skin pain, worsened psoriasis, skin blisters, bleeding skin, irritated skin, cracked skin, hair disorder, cold sores, inflammation of the skin, nail disorder, skin tightness, stinging skin, skin ulcers, worsened acne, vision disturbance, redness on the eyelid, eye infection, blood in the urine, painful menstruation, miscarriage, painful urination, increased menstruation, decreased urination, increased urination, urinary tract infection, inflammation of the vagina, allergic reactions, pancreatitis, elevations of serum triglycerides, hearing impairment, hepatotoxicity, inflammatory bowel disease, hyperostosis, vision impairment, and pregnancy. These adverse side effects may occur not only in a patient taking a retinoid, but also in fetus and issue of the patient. More specifically, the administration of retinoids, such as, for example, Tazarotene, are known or suspected of causing birth defects if taken by a pregnant woman. In addition, an active agent otherwise beneficial to a patient may have adverse side effects in individuals having specific pre-existing conditions or individuals concurrently taking other specific medications.

Thus, the delivery of active retinoid agents of low aqueous solubility in a form which is biologically available while preventing adverse side effects is of utmost important and the subject of the present invention. Methods have been developed for delivering an active agent to a patient while preventing adverse side effects, see for example, U.S. Pat. Nos. 6,045,501 and 6,315,720. However, these methods do not address the issue of enabling the delivery of an active agent which includes a means for solubilizing retinoids and insuring effective systemic delivery of a retinoid active agent.

SUMMARY OF THE INVENTION

In a preferred embodiment, the method of the present invention includes preparing doses of an active agent in the form of a capsule system for the oral delivery of an active agent having low aqueous solubility. The method includes an active retinoid agent having low aqueous solubility and a vehicle for eliminating any need for initial active agent dissolution within the gastro-intestinal tract. Such a capsule system is set forth in U.S. Pat. No. 6,248,354 B1.

More particularly, the vehicle may comprise a liquid triglyceride which fully dissolves the active agent. In this manner, initial active agent dissolution within the gastro-intestinal tract is not necessary, because it is initially dissolved in the vehicle.

In addition, an emulsifier provides a means for promoting self-emulsification of the active agent and the vehicle in the gastro-intestinal tract. In a preferred embodiment, a capsuled shell provides a means for encapsulating the active agent vehicle means and emulsifier. The capsuled shell is formulated to open or dissolve upon ingestion into the gastro-intestinal tract and accordingly release the active agent and vehicle. At this point, the self-emulsification occurs thereby facilitating absorption through the gastro-intestinal wall in order to provide biological availability and systemic circulation of the active agent.

Preferably, the vehicle comprises a medium chain liquid triglyceride which, as hereinabove noted, initially, fully dissolves the active retinoid agent. More particularly, the vehicle may comprise a caprylic/capric triglyceride and the emulsifier may comprise co-emulsifiers, such as sorbitan monooleate and polysorbate 80. Other vehicles which may be suitable include: Ethyl oleate, Isopropyl myristate, Cetearyl octanoate, Corn oil, Cottonseed oil, Safflower oil, Olive oil, Peanut oil, Soybean oil and Sesame oil. Other emulsifiers which may be suitable include: Sorbitan monolaurate, Sorbitan monopalmitate, Sorbitan monostearate and Polysorbates 20, 40 or 60.

Importantly, the co-emulsifiers are selected to match a hydrophilic/lipophilic balance (HLB) of the caprylic/capric triglyceride. This is important in order to promote the optimal emulsification of the triglyceride into the aqueous gastro-intestinal fluids and accordingly the absorption of the agent for systemic circulation.

More specifically, as hereinabove noted, the active retinoid agent may be Tazarotene and the vehicle further comprises an antioxidant, such as, for example, butylated hydroxyanisole. Other antioxidants which may be suitable include: Butylated hydroxytoluene, Tocopherols (Vitamin E), Propyl gallate, and Ascorbyl palmitate. Other active retinoid agents include, for example, Vitamin A and its natural and synthetic derivatives.

A capsuled shell, as hereinabove noted, further includes an opaque colorant to prevent degradation of a retinoid, such as Tazarotene, from exposure of the capsule system to harmful wavelength of light.

The method of the present invention includes the steps of providing an active retinoid agent having low aqueous solubility with the active agent dissolved in a vehicle in order to eliminate any need for initial active agent dissolution in the gastro intestinal tract.

The method further includes steps of incorporating an emulsifier to the vehicle in order to promote self-emulsification of the active agent and vehicle in the gastro-intestinal tract and the step of encapsulating the active agent, vehicle and emulsifier with a capsule shell formulated to open upon ingestion into the gastro-intestinal tract.

Steps in accordance with the method of the present invention further include distributing educational materials to medical office personnel including prescribers who are qualified to prescribe the doses to patients. The educational materials include information as to what the patients need to know and what the patients must do in order to avoid an adverse side effect while taking the doses and to receive a prescription for the doses. The method further includes providing guidelines for counseling the patients with regard to what the patients need to know and what the patients must do in order to avoid the adverse side effect while taking the dose and to receive prescriptions for the doses. More particularly, the method according to the present invention is applicable for active agents in which the adverse side effects includes at least one side effect selected from the group consisting of such side effects include weakness, rash, muscle pain, joint pain, joint disorder, increased blood levels of Creatine Phosphokinase, nose dryness, dizziness, nosebleed, dry eye, hair loss, elevated blood levels of fatty acids, increased muscle tone, anxiety, emotional instability, burning or tingling sensation to the skin, body pain, back pain, depression, diarrhea, acne, skin disorder, foot pain, abdominal pain, neck pain, dry mouth, dilated blood vessels, knee pain, infection, neck stiffness, pelvic pain, arm pain, chills, dandruff, leg pain, irregular heartbeat, increased blood pressure, migraine, fainting, increased heart rate, loss of appetite, gas, vomiting, stomach disorder, irritation in the mouth, purplish red spot on the skin, decreased number of blood platelets, abnormal white blood cell count, anemia, decrease in white blood cell count, abnormal platelets, increased cholesterol, increased blood levels of lactic dehydrogenase (the study doctor can explain this), swelling, thirst, protein in the urine, increased blood levels of amylase (the study doctor can explain this), bone pain, arthritis, bone disorder, muscle weakness, trouble sleeping, sleepiness, forgetfulness, sensing that either the body or the surroundings are moving, inflammation of the throat, inflammation in the nose, sore throat, inflammation of the sinus, skin redness from the sun, burning sensation on skin, skin burn, skin peeling, irritated skin, skin pain, worsened psoriasis, skin blisters, bleeding skin, irritated skin, cracked skin, hair disorder, cold sores, inflammation of the skin, nail disorder, skin tightness, stinging skin, skin ulcers, worsened acne, vision disturbance, redness on the eyelid, eye infection, blood in the urine, painful menstruation, miscarriage, painful urination, increased menstruation, decreased urination, increased urination, urinary tract infection, inflammation of the vagina, allergic reactions, pancreatitis, elevations of serum triglycerides, hearing impairment, hepatotoxicity, inflammatory bowel disease, hyperostosis, vision impairment, and pregnancy. Still, more particularly, the method in accordance with the present invention enables a delivery of Tazarotene.

In addition, the method in accordance with the present invention includes the distribution of educational materials to the prescribers and the method further comprises the step of requiring acknowledgment of receipt of the educational materials and guidelines from the prescribers and further may include the step of requiring acknowledgment of educational materials from the patients.

The method may further comprise the step of providing survey materials to the prescriber for distribution to the patients regarding what the patient needs to know about the adverse side effects while taking the doses and implementation by the patient of what the patient must do in order to avoid the adverse side effects while taking the doses and to receive prescriptions for the doses. In addition, the method may include the step of receiving completed surveys from the patient and advising the prescriber as to continuance or discontinuance of the prescribe doses for the patients.

Further, the method may also include the step of distributing prescribable doses to pharmacies and distributing educational materials to the pharmacies including pharmacists with the educational material including information as to what the patient needs to know and what the patients must do in order to both avoid the adverse side effects while taking the doses and to receive prescription doses from the pharmacists.

In addition, the method may include the step of providing guidelines to the pharmacists for counseling the patient with regard to what the patient needs to know and what the patient must do in order to both avoid the adverse side effect while taking the dose and to receive doses from the pharmacists. The method may further include the step of requiring acknowledgment of receipt of the educational materials and guidelines from the pharmacists and further acknowledgement of receipt of the educational materials by the patient from the pharmacists.

The method may also include the distribution of educational materials which are age and sex appropriate and include at least materials selected from the group consisting of video tapes, audio tapes, CDs, brochures and line drawings. The method may further comprise the step of orchestrating focus groups for patients with regard to what the patient needs to know and what the patient must do in order to avoid the adverse side effects and to receive prescription doses and further may include the step of requiring proof of attendance of the focus groups by the patient in order to receive initial or continued doses.

BRIEF DESCRIPTION OF THE DRAWINGS

The present invention may be more clearly understood with reference to the following detailed description in conjunction with the appended drawing, of which.

DETAILED DESCRIPTION

Figure 1:
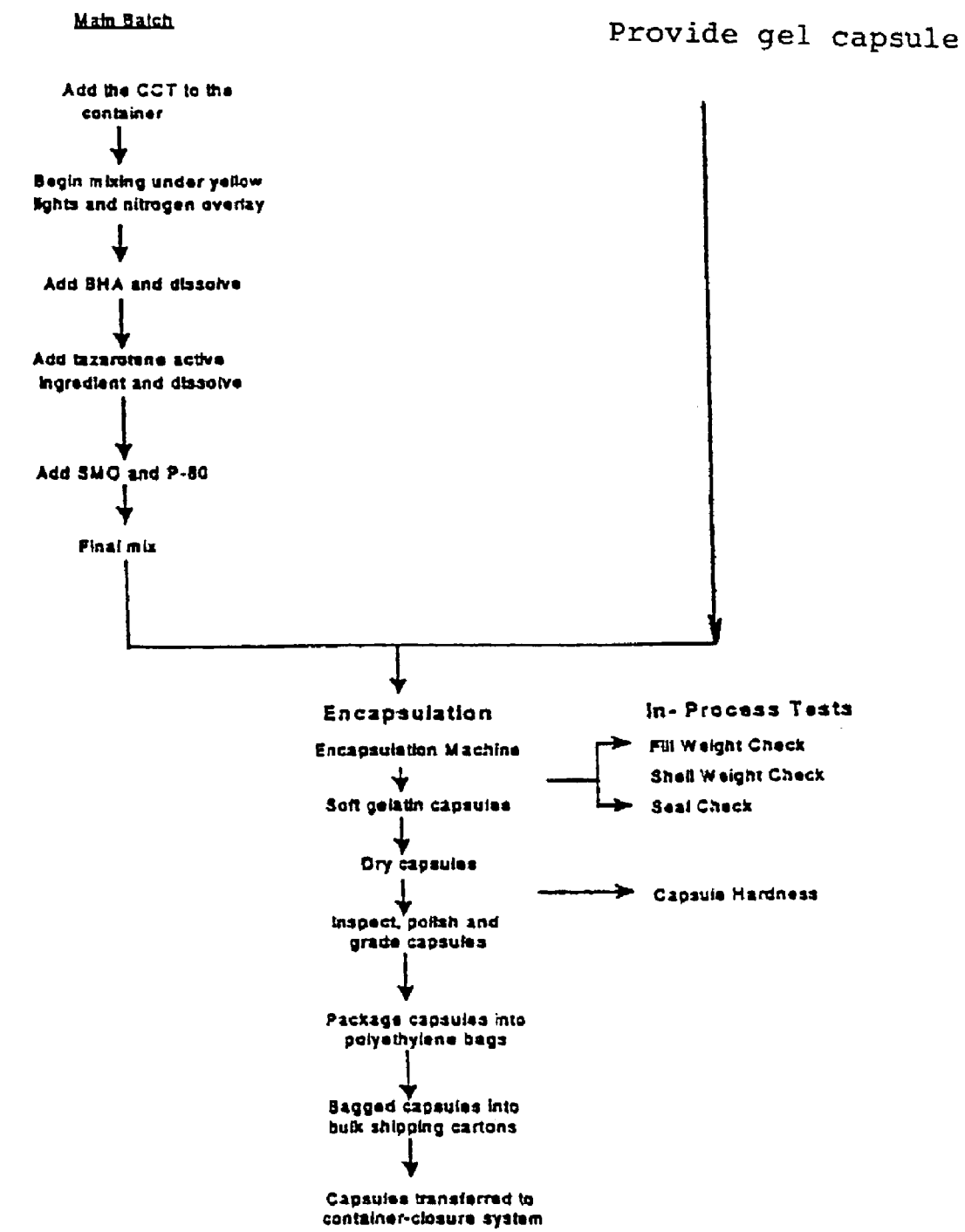
FIG. 1 is a manufacturing process flow chart for the capsule system in accordance with the present invention.

The present invention includes a capsule systems for the delivery of active agents, particularly retinoids. In a preferred example, it is known that the compound Tazarotene, known chemically as ethyl 6-[(4,4-dimethylthiochroman-6-yl)ethynyl]-nicotinate, having the molecular formula $C_{21}H_{21}NO_2S$, is active in the treatment of acne and psoriasis. Substantially increased activity of the active agent in this regard is expected if oral delivery can be effected. However, the solubility of Tazarotene in water is negligible.

The capsule of the present invention takes advantage of the Tazarotene property of rapid systemic elimination (see $t_{1/2}$ in table II), not exhibited by other currently available retinoids for acne and psoriasis, such as isotretinoin, acitretin, and etretinate. The capsule of the present invention provides high and reliable oral absorption of Tazarotene thus it produces effective therapeutic concentrations in man upon oral ingestion. The rapid system elimination is important for many patients, especially for women of child-bearing age. Upon cessation of oral Tazarotene treatment, Tazarotene is rapidly cleared from the body and poses little risks of teratogenic effects. The typical precautionary pregnancy wash-out periods for women of child-bearing age who just got off treatment of isotretinoin, acitretin, and etretinate are one month, three years, and for indefinite period of time, respectively.

In general, a capsule system in further accordance with the present invention includes a soft gelatin capsule containing an active retinoid having low aqueous solubility, such as Tazarotene, which is fully solubilized in a liquid trigylceride solution. The gelatin in accordance with the present invention may be derived from bovine sources which provides a capsule shell plasticized by, for example, glycerin.

Any suitable capsule shell formulation may be utilized which provides a means for not only encapsulating the retinoid active agent, but also for releasing same upon ingestion into a gastro-intestinal tract. It should also be appreciated that the system in accordance with the present invention may also contain conventional additional adjuvant substances which are conventionally used in the manufacture of drug capsules for providing consistency or facilitate the manufacture of the capsule. A lipophilic vehicle, such as a medium chain trigylceride, and more specifically a caprylic/capric triglyceride is provided for active agent dissolution.

Importantly, the retinoid agent, Tazarotene, is fully dissolved in the vehicle in a conventional manner before incorporation into the capsule shell. The total dissolution of Tazarotene in the vehicle facilitates absorption from the gastro-intestinal tract by eliminating the need for drug dissolution prior to absorption. Utilizing caprylic/capric triglyceride has been found that up to about 34 mg of Tazarotene can be effectively solubilized in a capsule.

In other words, the Tazarotene is made particularly biological available and can be absorbed by the body, although it is hard to dissolve in aqueous solutions, such as gastric juices.

Emulsifier means in accordance with the present invention is provided for promoting self-emulsion of the active agent and the vehicle in the gastro-intestinal tract. Preferably, emulsifier means includes a co-emulsifier system which matches the HLB requirements of the medium chain triglyceride, i.e., caprylic/capric triglyceride. This self-emulsion occurs in the gastro-intestinal tract following the gelatin shell opening.

More specifically, the co-emulsifier system includes sorbitan monooleate NF, and polysorbate 80 NF, which are commercially available.

Butylated hydroxyanisole NF (also commercially available), is added as an antioxidant to stabilize the Tazarotene. In addition, a colorant, such as, for example, titanium dioxide, is added to the shell formulation in order to provide protection of the Tazarotene from light which may otherwise cause degradation thereof. Otherwise, the shell may be conventionally formed of, for example, Gelatin and Glycerin.

The composition of two representative strengths of Tazarotene soft gelatin capsules is shown in Table 1.

A person skilled in the art would appreciate that the composition of the fill formulation shown in Table 1 may be altered somewhat to optimize the solubilization and/or emulsification of the drug. Additionally, the person of skill in the art would appreciate that the capsule systems and fill formulations disclosed herein would be suitable for retinoids other than Tazarotene.

TABLE 1

| | | Concentration (mg/capsule) | |
| --- | --- | --- | --- |
| INGREDIENT | FUNCTION | 0.7 mg Soft Gelatin Capsule (9096X) | 0.2 mg Soft Gelatin Capsule (9154X) |
| Fill Formulation: | | | |
| Tazarotene | Active | 0.70 | 0.20 |
| Butylated Hydroxyanisole NF | Anti-oxidant | 0.05 | 0.05 |
| Sorbitan Monooleate NF | Emulsifier | 5.0 | 5.0 |
| Polysorbate 80 NF | Co-emulsifier | 0.25 | 0.25 |
| Medium-chain Triglycerides EP | Lipophilic vehicle | 94.0 | 94.5 |

Manufacturing Description with reference to FIG. 1.

The manufacture of the drug product involves three major manufacturing stages:

1. The manufacture of the triglyceride-based fill formulation.

2. Providing a gelatin capsule shell.

3. Soft gelatin encapsulation.

Details of each manufacturing stage is described in the following sections.

Manufacturing Directions

Manufacture of the Triglyceride-Based Fill Formulation
1. Caprylic/capric triglyceride (CCT), which is a medium chain triglyceride, is weighed and added into a suitable mixing container.
2. Under yellow lights and a blanket of nitrogen, the following ingredients are added to the CCT while mixing, allowing each to fully dissolve before adding next:
  Butylated Hydroxyanisole
  Tazarotene (active pharmaceutical ingredient)
3. The following ingredients are then weighed and added sequentially.
  Polysorbate 80(P-80)
  Sorbitan Monooleate (SMO)
4. The resulting bulk solution is mixed until homogeneous.
5. The batch is then encapsulated using the procedure described in Soft Gelatin Encapsulation.

Soft Gelatin Encapsulation
1. The encapsulation machine is of the rotary die type. It is fed by two receivers, one contains the molten gelatin mass used to form the shell, while the other contains the fill formulation.
2. The encapsulation machine provides a continuous form, fill, and seal operation.
   a. The molten gelatin mass flows by gravity through heated tubes to two heated spreader boxes. The spreader boxes simultaneously cast the gelatin mass into two ribbons. These are lubricated with a blend of fractionated coconut oil/lecithin and delivered to the rotary dies.
   b. The fill formulation flows by gravity into a hopper which serves as a reservoir to the input of the encapsulation pump. The fill formulation is delivered to the filling point by the positive displacement piston pump.
   c. The two gelatin ribbons are fed in between the two rotating dies. The dies contain paired pockets which form the shape of the soft gelatin capsule and provide the sealing mechanism. At the precise moment that the two die pockets line up, the fill formulation is injected through an encapsulation wedge in between the gelatin ribbons. The seal forms as a result of the pressure between dies and heat applied by the encapsulation wedge to produce the soft gelatin capsule.
3. The capsules are then dried by a two phase process:
   a. The capsules are moved to a rotary drier attached to the encapsulation machine. They are tumbled in a warm, low humidity, forced air environment for a predetermined length of time as specified in the batch records.
   b. The second phase begins after discharge from the rotary drier. The capsules are spread in a monolayer on shallow drying trays and low humidity air passed over them. Transfer of water to and from the shell occurs over several days until the water put into the gelatin during gelatin mass production has evaporated.
   c. Capsule hardness determinations are performed to monitor the drying process. The capsules are monitored until the hardness is within the specified range. The capsules are then placed into deep holding trays.
4. Capsules are inspected and polished with V.M. & P Naphtha to remove the lubricating film on the capsule surface, prior to grading and packaging.

Tazarotene soft gelatin capsules with the formulation set forth in Table 1 have currently been shown to be physically and chemically stable through twelve months of storage at 25° C. as well as a six months storage at 40° C.

Table II, shows the plasma concentration of Tazarotene following dosing of the capsules set forth in Table I.

The results shown indicate effective levels of Tazarotene in plasma immediately following ingestion of the drug capsule system in accordance with the present invention when taken with and without a liquid nutritional supplement that simulates food. These plasma concentration levels may be sufficient to effect a treatment of acne in a patient.

The methods of the present invention are especially advantageously when employed for the delivery of a teratogenic active agent, such as Tazarotene, hereinabove described. Accordingly, in one embodiment of the present invention, a method provides for enabling delivery of Tazarotene while avoiding administration of Tazarotene (also known as Tazorac®) to pregnant women.

Methods of the present invention provide for Pregnancy Avoidance Contraception on Tazorac® (PACT).

Generally speaking, the methods of the present invention may be desirably advantageously used to:
  counsel females of childbearing potential about the risk of serious birth defects or miscarriage if the

TABLE II

Tazarotene Dosage Equivalents and Steady-State Pharmacokinetic Parameters of Tazarotenic Acid in Healthy Subjects

| Treatment | Dosage[1] (mg/kg/day) | Dosage[1] (mg/kg/day) | $C_{max}$ | $t_{max}$ | AUC |
|---|---|---|---|---|---|
| 0.2 mg/day (with Ensure ®) | 0.003 | 0.12 | 5.24 = 2.27 | 3.67 = 1.51 | 30.6 |
| 0.7 mg/day (with Ensure ®) | 0.010 | 0.40 | 19.9 = 6.6 | 2.83 = 0.98 | 101 |
| 0.7 mg/day (with water ®) | 0.010 | 0.40 | 18.9 = 4.6 | 3.00 = 1.55 | 94.1 |
| 1.4 mg/day (with Ensure ®) | 0.020 | 0.81 | 36.6 = 8.5 | 1.83 = 0.75 | 179 |
| 2.1 mg/day (with Ensure ®) | 0.030 | 1.21 | 44.3 = 13.9 | 4.17 = 2.04 | 219 |

Notes: Preliminary data following 5 days of once daily dosing are presented.
[1] = Assumes average subject weighs 70 kg and has surface area of 1.73 m$^2$
[2] = Effective half-life; harmonic mean and pseudo-standard deviation reported.
[3] = Not calculable
Ensure ® is a liquid nutritional supplement that simulates food.

investigational drug, Tazorac® (tazarotene) capsules are taken during pregnancy;

provide an opportunity once the informed consent form has been reviewed and signed (during the screening (Day-30 to −2) through qualification, (Week 0) visit period) for the patient to:

read and discuss the patient brochure entitled P.A.C.T.™ Pregnancy Avoidance and Contraception on Tazorac®, *What Women Need to Know*, and, view and discuss the video or CD-ROM entitled P.A.C.T.™ Pregnancy Avoidance and Contraception on Tazorac®;

reinforce the required birth control methods to help ensure pregnancy is avoided while on a clinical study of tazarotene capsules. Review the patient's choices to assure they meet the study criteria and confirm that required birth control has been implemented for at least 28 days prior to study enrollment. Remind patients to advise their doctor if they decide to change birth control methods during the study course;

reinforce that it is the patient's responsibility to avoid pregnancy by following the study requirements for pregnancy prevention;

conduct pregnancy testing according to the protocol schedule assuring that tazarotene capsules are not dispensed if the patient is found to be pregnant;

remember that the first time in which tazarotene capsules are dispensed is during a woman's menstrual period;

remind abstinent patients that they must advise their doctor of the birth control methods they will use during the study if they were to become sexually active;

instruct patients regarding the availability of emergency contraception and the need to contact their doctor if they were to have sexual intercourse without using the two required birth control methods, or, if they feel their contraceptive method may have failed, i.e., condom broke, diaphragm slipped;

encourage patients to participate in a confidential P.A.C.T.™ Survey.

More specifically, the methods in accordance with the present invention provide for distributing educational materials to medical office personnel including prescribers who are qualified to prescribe the doses for patients. The term, office personnel, further includes paramedics, clerks, nurses and other employees of a physicians office, hospital or medical unit. The term, prescriber, refers to any individual who is able to prescribe drugs as, for example, a medical doctor.

The educational materials preferably include items useful in the counseling of the patient and include, but not limited to, a video tapes, audio tapes, DVDs, CDs, brochures, photographs and other drawings for describing risks and benefits associated with taking the active agents, measures which may be taken to avoid such risks and counseling techniques and advice for the patients.

Education materials preferably include information in contraceptive choices, such as, for example, continuous or periodic abstinence, Outercourse in which sex play is conducted without vaginal intercourse, withdrawal by the male sex partner to prevent the sperm from joining an egg, sterilization, which includes an operation to keep the sperm from joining an egg, hormonal treatment, such as NORPLANT® to prevent a release of an egg and thicken cervical mucus to keep sperm from joining the egg, an intra-uterine device (IUD) an estrogen/progesterone pill, the use of condoms and diaphragm or cervical caps, the use of a female condom or spermicide as well as information on emergency conception, such as, for example, emergency IUD insertion within five days of unprotected intercourse or emergency contraceptive pills.

In accordance with the methods of the present invention, guidelines are provided for counseling the patients with regard to what the patients need to know and what the patients must do in order to avoid the adverse side effects, including pregnancy, while taking the dose and to receive prescriptions for the doses.

These guidelines include, but are not limited to obtaining a history from the patient by asking key questions to determine if the patient has been sexually active, and for a determination of the level of contraceptive knowledge and experience. Guidelines are provided for determining patient ability to comply with contraceptive measures.

Such counseling and guidelines should include instruction that the patient may respond to questions in a manner avoiding what the individual's sexual activity has been or should be. The counselor should also be alerted to the fact that the patient may respond consistent with what the patient thinks that the counselor wants to hear in contrast to what is the true facts of the patients sexual activity and pregnancy status.

Guidelines are provided for honing the skills of the counselor, which may be the prescriber, for assessing the patients response and improving communication with the patient.

Nonverbal clues, such as, eye contact, uneasiness, body movements, and general demeanor provide behaviors for which the guidelines are addressed. Guidelines further set forth the establishment of whether the patient fully understands the questions and also providing an environment which is conducive for the patient to be truthful in answering questions.

Such counseling and guidelines may include the isolation of the patient from, for example, parents if the patient is a teenager. In that regard, both the educational materials and guidelines provided under the method of the present invention are preferably age and sex appropriate.

For encouraging both prescriber and patient compliance the method in accordance with the present invention preferably comprises the step requiring acknowledgment of receipt of the educational materials from the prescriber and patient and further acknowledgment of receipt of the guidelines from the prescribers.

In furtherance of patient compliance, the method according to the present invention further may include the step of providing survey materials to the prescribers for distribution to the patients regarding what the patients need to know about the adverse side effects while taking the doses and implementation by the patient of what the patient must do in order to prevent the adverse effect while taking the doses and to receive prescriptions for the doses.

Such as survey materials preferably include questions regarding patient materials and instruction such as but not limited to:

Was the patient reminded about the risk of serious birth defects or miscarriages while taking the study medication; and importance of avoiding pregnancy while taking the study medication. Was the patient reminded about the need to use two effective forms of birth control such as hormonal pill, hormonal implant, tubal ligation, vasectomy, IUD; condom, diaphragm, cervical cap, spermicide. Was the patient instructed not to become pregnant until after the patient's last study visit.

Questions regarding study medication status such as: is the patient taking the study medication and if they are currently participating in the study; questions regarding continuing treatment, such as if a urine pregnancy test was performed before the patient received a new package of study medication.

Survey material further should include questions such as birth control methods used, such as what type(s) of birth control the patient is currently using such as tubal ligation, vasectomy, Depo-Provera® Injection, oral contraceptive, IUD, rhythm method, diaphragm, cervical cap, latex condoms, Norplant®, spermicide, abstinence, none or other; if the patient's doctor indicated that for medical reasons the patient must use barrier methods only; if the patient is having sexual intercourse and if they are that they are using the required birth control methods every time the patient had sexual intercourse since the screening visit; if the patient missed their period or if their period is late; if the patient is pregnant; if the patient is pregnant, if they had a pregnancy test and if the pregnancy test is positive; questions regarding study medication and pregnancy, such as the patient should not become pregnant while taking study medication; that the patient should not become pregnant during the study; that the patient should not become pregnant until at least one menstrual cycle passes following the end of treatment; that the patient should have sexual intercourse while using two effective forms of birth control and that emergency contraception is available.

The method in accordance with the present invention further preferably includes the step of receiving completed surveys from the patients and advising the prescribers as to the continuance and/or discontinuance of prescribing the doses for-the patients.

Further, enablement of drug delivery may include the step of distributing educational materials to pharmacies including pharmacy personnel, such as, pharmacists, with the educational materials, with the educational materials including information as to what the patients need to know and what the patients must do in both avoid adverse side effects while taking the doses and receive the prescription dose from the pharmacists, such educational materials are being hereinabove described.

In addition, the present method may include the step for providing guidelines to the pharmacists for counseling the patients as hereinabove noted. Preferably, the method includes the step of requiring acknowledgment receipt of the educational materials and guidelines from the pharmacists and further acknowledgement of receipt of educational materials by the patient from the pharmacists.

In order to assess the perceived knowledge of the patient through the distributed educational materials and counseling the method in accordance with the present invention may further comprise the step orchestrating focus groups for potential patients with regard to what the potential patient needs to know and what the patient must do in order to avoid the adverse side effects.

Educational materials may be distributed, counseling provided to the potential patients and thereafter personal surveys or written surveys may be conducted in order to determine whether the educational materials and the guidelines have correctly perceived.

Optionally, the method in accordance with the present invention may include the step or orchestrating focus groups for the patients with regard to what the patient needs to know and what the patient must do in order to both avoid the adverse side effects and assessing to perceive knowledge of the patient before the patient receives a prescription for the doses. In that, regard the method in accordance with the present invention may further provide the step of requiring proof of focus group attendance by the patients in order for the patient to receive doses.

Although there has been hereinabove described a method for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. An improvement to a method for enabling delivery of Tazarotene, the method comprising the steps of:
   manufacturing a fill formulation by dissolving Caprylic/Capric Triglyceride (CCT) butylated hydroxytoluene and hereafter dissolving the Tazarotene thereinto;
   adding Polysorbate 80 and Sorbiton Monooleate to the CCT, butylated hydroxyanide, and Tazarotene to form a bulk solution;
   mixing the bulk solution until homogeneous; and
   encapsulating the homogeneous bulk solution into a capsule,
   said improvement comprising:
   distributing educational materials to medical office personnel including prescribers who are qualified to prescribe the capsules for patients, said educational materials including information as to what the patients need to know and what the patients must do in order to both avoid adverse side effects while taking the capsules and to receive a prescription for the capsules; and
   providing guidelines for counseling the patients with regard to what the patients need to know and what the patients must do in order to both avoid the adverse side effect while taking the capsules and to receive prescriptions for the capsules.

2. The improvement according to claim 1 wherein the guidelines are provided to the prescribers and the improvement further comprises the step of requiring acknowledgment of receipt of the educational materials and guidelines from the prescribers.

3. The improvement according to claim 2 further comprising the step of requiring acknowledgment of education materials from the patient.

4. The method according to claim 3 further comprising the step of providing survey materials to the prescribers for distribution to the patients regarding what the patients need to know about the adverse side effect while taking the capsules and implementation by the patient of what the patient must do in order to avoid the adverse effect while taking the capsules and to receive prescription for the capsules.

5. The improvement according to claim 4 further comprising the step of receiving completed surveys from the patient and advising the prescribers as to continuance and discontinuance of prescribing capsules for the patients.

6. The improvement according to claim 1 further comprising the step of distributing the capsules to pharmacies.

7. The improvement according to claim 6 further comprising the step of distributing educational material to the pharmacy personnel including pharmacists, said educational materials including information as to what the patients need to know and what the patients must do in order to both avoid the adverse side effect while taking the capsules and to receive the capsules from the pharmacist.

8. The improvement according to claim 7 further comprising the step of providing guidelines to the pharmacist for counseling the patients with regard to what the patient needs to know and what the patient must do in order to both avoid the adverse side effect while taking the capsules and to receive capsules from the pharmacist.

9. The improvement according to claim 8 further comprising the step of requiring acknowledgment of receipt of the education materials and guidelines from the pharmacist.

10. The improvement according to claim 9 further comprising the step of requiring acknowledgment of receipt of the education materials by the patient from the pharmacist.

11. The improvement according to claim 1 wherein said education materials are age and sex appropriate.

12. The improvement according to claim 11 wherein said education materials are selected from the group consisting of video tape, audio tape, CDs, brochures and line drawings.

13. The improvement according to claim 1 further comprising the step of orchestrating focus groups for potential patients with regard to what the potential patient need to know and what the patient must do in order to both avoid the adverse side effect and assessing the perceived knowledge of the potential patient.

14. The improvement according to claim 1 further comprising the step of orchestrating focus groups for patients with regard to what the patient need to know and what the patient must do in order to both avoid the adverse side effect and to receive a prescription for the capsules.

15. The improvement according to claim 14 further comprising the step of requiring proof of focus group attendance by the patient in order for the patient to receive capsules.

16. An improvement to a method for enabling delivery of an active agent having low aqueous solubility, the method comprising the steps of:
    providing an active retinoid agent having low aqueous solubility consisting of Tazarotene;
    dissolving the active agent in a vehicle in order to eliminate initial active agent dissolution within a gastrointestinal tract;
    incorporating an emulsifier into the vehicle in order to promote subsequent self-emulsion of the active agent in a vehicle in the gastrointestinal tract;
    encapsulating an active agent, vehicle, and emulsifier with a capsule shell formulated to open upon ingestion into said gastrointestinal tract; and
    drying the capsule shell to obtain a selected hardness, said improvement comprising:
    distributing educational materials to prescribers who are qualified to prescribe the capsules for patients, said educational materials including information as to what the patients need to know and what the patients must do in order to both avoid adverse side effect while taking the capsules and to receive a prescription for the capsules;
    providing guidelines for counseling the patients with regard to what the patients need to know and what the patients must do in order to both avoid the adverse side effect while taking the capsules and to receive prescriptions for the capsules;
    requiring acknowledgment of receipt of the educational materials and guidelines;
    providing survey materials to the prescribers for distribution to the patients regarding what the patients need to know about the adverse side effect avoidance while taking the capsules and implementation by the patient of what the patient must do in order to avoid the adverse side effect while taking the capsules and to receive prescriptions for the capsules;
    receiving completed surveys from the patents; and
    advising the prescribers as continuance and discontinuance of prescribing capsules for the patients.

17. The improvement according to claim 16 further comprising the step of distributing capsules to pharmacies.

18. The improvement according to claim 17 further comprising the step of distributing educational materials to the pharmacy personnel including pharmacists, said educational materials including information as to what the patients need to know and what the patients must do in order to both avoid the adverse side effect while taking the capsules and to receive the prescription capsules from the pharmacist.

19. The improvement according to claim 18 further comprising the step of providing guidelines to the pharmacist for counseling the patients with regard to what the patient needs to know and what the patient must do in order to both avoid the adverse side effect while taking the capsules and to receive capsules from the pharmacist.

20. The improvement according to claim 19 further comprising the step of requiring acknowledgment of receipt of the education materials and guidelines from the pharmacist.

21. The improvement according to claim 20 further comprising the step of requiring acknowledgment of receipt of the education materials by the patient from the pharmacist.

22. The method according to claim 16 wherein said education materials are age and sex appropriate.

23. The improvement according to claim 16 further comprising the step of orchestrating focus groups for potential patients with regard to what the patient need to know and what the patient must do in order to both avoid the adverse side effect and assessing the perceived knowledge of the potential patient.

24. The improvement according to claim 16 further comprising the step of orchestrating focus groups for patients with regard to what the patient need to know and what the patient must do in order to both avoid the adverse side effect and assessing the perceived knowledge of the patient before providing a prescription for the capsules.

25. The improvement according to claim 24 further comprising the step of requiring proof of focus group attendance by the patient in order for the patient to receive capsules.

* * * * *